(12) United States Patent
Tybinkowski et al.

(10) Patent No.: US 9,016,941 B2
(45) Date of Patent: *Apr. 28, 2015

(54) ANATOMICAL IMAGING SYSTEM WITH A CRAWL DRIVE

(75) Inventors: Andrew P. Tybinkowski, Boxford, MA (US); Eric M. Bailey, Hampton, NH (US); Daniel Allis, Lynn, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,668

(22) Filed: Aug. 24, 2012

(65) Prior Publication Data

US 2013/0202094 A1 Aug. 8, 2013

Related U.S. Application Data

(63) Continuation of application No. 12/655,360, filed on Dec. 29, 2009, now Pat. No. 8,251,584, which is a continuation of application No. 11/706,133, filed on Feb. 13, 2007, now Pat. No. 7,637,660, which is a continuation of application No. 11/193,941, filed on Jul. 29, 2005, now Pat. No. 7,175,347.

(60) Provisional application No. 60/670,164, filed on Apr. 11, 2005, provisional application No. 60/593,001, filed on Jul. 30, 2004.

(51) Int. Cl.
*A61B 6/00* (2006.01)
*A61B 6/03* (2006.01)
*A61B 6/04* (2006.01)
*G01N 23/04* (2006.01)

(52) U.S. Cl.
CPC .............. *A61B 6/4405* (2013.01); *A61B 6/032* (2013.01); *A61B 6/04* (2013.01); *A61B 6/4488* (2013.01); *A61B 6/501* (2013.01); *G01N 23/046* (2013.01); *G01N 2223/419* (2013.01); *G01N 2223/612* (2013.01)

(58) Field of Classification Search
CPC ........ A61B 6/4405; A61B 6/032; A61B 6/04; A61B 6/4488; A61B 6/501; G01N 23/046; G01N 2223/419; G01N 2223/612
USPC ...................... 378/4, 19, 20, 62, 64, 196–198
See application file for complete search history.

(56) References Cited

U.S. PATENT DOCUMENTS

| | | | |
|---|---|---|---|
| 3,603,975 A | | 9/1971 | Gordon |
| 3,775,612 A | * | 11/1973 | Foster et al. ................... 378/60 |
| 3,904,878 A | * | 9/1975 | Burch et al. ................... 378/60 |
| 4,006,359 A | * | 2/1977 | Sullins et al. .................. 378/60 |
| 4,131,802 A | | 12/1978 | Braden et al. |
| 4,928,283 A | | 5/1990 | Gordon |

(Continued)

FOREIGN PATENT DOCUMENTS

| | | |
|---|---|---|
| CN | 1037450 | 11/1989 |
| JP | 11-164829 | 6/1999 |

(Continued)

*Primary Examiner* — Irakli Kiknadze
(74) *Attorney, Agent, or Firm* — Pandiscio & Pandiscio

(57) ABSTRACT

An imaging system for imaging an object, comprising a scanner; and a transport mechanism mounted to the base of the scanner, wherein the transport mechanism comprises a crawl drive for crawling along the floor supporting the imaging system so as to index the scanner relative to an object during scanning of the object.

16 Claims, 25 Drawing Sheets

(56) References Cited

U.S. PATENT DOCUMENTS

| | | | |
|---|---|---|---|
| 5,448,607 A | 9/1995 | McKenna | |
| 5,867,553 A | 2/1999 | Gordon et al. | |
| 5,887,047 A | 3/1999 | Bailey et al. | |
| 5,982,843 A | 11/1999 | Bailey et al. | |
| 6,108,396 A | 8/2000 | Bechwati et al. | |
| 6,144,180 A * | 11/2000 | Chen et al. | 318/587 |
| 6,212,251 B1 * | 4/2001 | Tomura et al. | 378/15 |
| 6,256,404 B1 | 7/2001 | Gordon et al. | |
| 6,285,028 B1 | 9/2001 | Yamakawa | |
| 6,374,937 B1 | 4/2002 | Galando et al. | |
| 6,396,902 B2 | 5/2002 | Tybinkowski et al. | |
| 6,459,923 B1 | 10/2002 | Plewes et al. | |
| 6,705,758 B1 * | 3/2004 | Luusua et al. | 378/198 |
| 6,813,374 B1 | 11/2004 | Karimi et al. | |
| 6,857,778 B2 * | 2/2005 | Mun et al. | 378/206 |
| 6,959,068 B1 * | 10/2005 | Sommer | 378/20 |
| 7,319,738 B2 | 1/2008 | Lasiuk et al. | |
| 7,338,207 B2 | 3/2008 | Gregerson et al. | |
| 8,118,488 B2 | 2/2012 | Gregerson | |
| 2002/0035317 A1 | 3/2002 | Cheng et al. | |
| 2003/0072613 A1 * | 4/2003 | Colvard | 404/105 |
| 2003/0095635 A1 | 5/2003 | Moritake et al. | |
| 2005/0284672 A1 * | 12/2005 | Egen et al. | 180/65.1 |
| 2007/0183588 A1 | 8/2007 | Bailey et al. | |
| 2007/0183589 A1 | 8/2007 | Tybinkowski et al. | |
| 2007/0195938 A1 | 8/2007 | Bailey et al. | |
| 2010/0172468 A1 | 7/2010 | Gregerson | |
| 2011/0222667 A1 | 9/2011 | Gregerson et al. | |
| 2011/0228910 A1 | 9/2011 | Gregerson et al. | |
| 2012/0256099 A1 | 10/2012 | Gregerson et al. | |
| 2012/0330087 A1 | 12/2012 | Gregerson | |

FOREIGN PATENT DOCUMENTS

| | | |
|---|---|---|
| JP | 2003-190149 | 7/2003 |
| WO | WO 98/00681 | 1/1998 |

* cited by examiner

ANATOMICAL IMAGING SYSTEM WITH A CRAWL DRIVE

REFERENCE TO PENDING PRIOR PATENT APPLICATIONS

This patent application is a continuation of prior U.S. patent application Ser. No. 12/655,360, filed Dec. 29, 2009 now U.S. Pat. No. 8,251,584 by Andrew P. Tybinkowski et al. for ANATOMICAL IMAGING SYSTEM WITH CENTIPEDE BELT DRIVE, which in turn is a continuation of prior U.S. patent application Ser. No. 11/706,133, filed Feb. 13, 2007 now U.S. Pat. No. 7,637,600 by Andrew P. Tybinkowski et al. for ANATOMICAL IMAGING SYSTEM WITH CENTIPEDE BELT DRIVE, which in turn is a continuation of prior U.S. patent application Ser. No. 11/193,941, filed Jul. 29, 2005 now U.S. Pat. No. 7,175,347 by Andrew P. Tybinowski et al. for ANATOMICAL IMAGING SYSTEM WITH CENTIPEDE BELT DRIVE, which in turn claims benefit of:

(i) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE; and (ii) prior U.S. Provisional Patent Application Ser. No. 60/593,001, filed Jul. 30, 2004 by Bernard Gordon et al. for ANATOMICAL SCANNING SYSTEM.

The above-identified patent applications are hereby incorporated herein by reference.

FIELD OF THE INVENTION

This invention relates to anatomical imaging systems in general, and more particularly to anatomical imaging systems of the sort utilizing Computerized Tomography (CT) systems and the like.

BACKGROUND OF THE INVENTION

Strokes are the third leading cause of death in the United States (causing approximately 17,000 deaths per year) and the number one cause of long-term disability (affecting nearly 5 million people). Strokes result from abrupt damage to the brain or spinal cord caused by an abnormality of the blood supply.

Strokes typically occur in one of two forms: (i) hemorrhagic which occurs with the rupture of a blood vessel; and (ii) ischemic, which occurs with the obstruction of a blood vessel.

Rapid diagnosis is a key component of stroke management. This is because treatments for ischemic strokes may be contra-indicated for treatment of hemorrhagic strokes and, furthermore, the effectiveness of a particular treatment can be time-sensitive. In particular, the only approved therapy for acute ischemic strokes, i.e., the administration of tPA to eliminate clots, is contra-indicated for hemorrhagic strokes. Furthermore, tPA is most effective if it is administered within 3 hours of the onset of an ischemic stroke. However, current diagnosis times (i.e., the time needed to identify that the patient is suffering from a stroke and to identify the hemorrhagic or ischemic nature of the stroke) frequently exceeds this 3 hour window. As a result, only a fraction, of ischemic stroke victims are properly treated with tPA.

Imaging is generally necessary to: (i) distinguish strokes from other conditions; (ii) distinguish between the different types of strokes (i.e., hemorrhagic or ischemic); and (ii) determine suitable treatments. Computerized Tomography (CT) has emerged as the key imaging modality in the diagnosis of strokes. CT scans, including Non-Enhanced CT, CT angiography and CT perfusion, provide the necessary and sufficient information for diagnosing and treating strokes.

Unfortunately, however, the "round-trip" time between the emergency room (where the patient is typically first received) and the radiology department (where the CT machine is typically located) can frequently take up to several hours, even in the best hospitals. As a result, the time spent in transporting the patient from the emergency room to the CT machine and back again can consume critical time which can compromise treatment of the patient.

Thus, there is a need for a new and improved CT machine which is particularly well suited for use in stroke applications.

SUMMARY OF THE INVENTION

The present invention comprises a new and improved anatomical imaging system which addresses the foregoing problems. More particularly, the present invention comprises a small, mobile CT machine that can be moved to the patient so that the patient can be scanned at their current location, thus dramatically reducing diagnostic times. The mobile CT machine can be located in the emergency room, is easy to transport directly to the patient's bedside, and provides image quality favorably comparable to traditional, fixed-location CT machines which require patient transport.

In essence, the new CT machine eliminates traditional transportation delays by allowing patients to be scanned in the emergency room, while remaining on their gurney.

More particularly, with a conventional CT machine, the CT machine is fixed in place, typically in the radiology department. The patient is moved to the CT machine, placed on a precision-advancement patient platform and then, with the scanning apparatus remaining stationary, the patient is advanced into the scanning zone of the CT machine using the precision-advancement patient platform. In contrast, with new CT machine of the present invention, the patient remains in the emergency room on their gurney, the CT machine is moved to the patient and then, while the patient remains stationary, the CT machine is precision-advanced relative to the patient so that the scanning zone of the CT machine moves relative to the patient. Thus, the new CT machine of the present invention can be wheeled into position in an emergency room and the patient scanned while remaining on their gurney, without ever having to move the patient from the emergency room to the radiology department, and then off the gurney and onto the moving platform of a traditional, fixed-location CT machine.

As a consequence of this novel approach to CT scanning, the new CT machine requires a precision-advancement mechanism for moving the entire CT machine relative to the patient during the scanning process.

To this end, the present invention provides a novel centipede belt drive which provides high precision movement of the CT machine relative to the patient during scanning. In particular, the centipede belt drive is designed to provide substantially the same degree of precision when moving the CT machine about the patient as conventional CT machines provide when moving the precision-advancement patient platform relative to the fixed scanning zone of the conventional CT machine.

Preferably the novel CT machine comprises two transport mechanisms: one for moving the CT machine relatively quickly across room distances prior to scanning, and one for moving the CT machine precisely relative to the patient during scanning.

In one preferred form of the invention, there is provided an anatomical imaging system comprising:
a CT machine; and
a transport mechanism mounted to the base of the CT machine, wherein the transport mechanism, comprises a fine movement mechanism for moving the CT machine precisely, relative to the patient, during scanning.

In another preferred form of the invention, there is provided an anatomical imaging system comprising:
a CT machine; and
a transport mechanism mounted to the base of the CT machine, wherein the transport mechanism comprises:
a gross movement mechanism for transporting the CT machine relatively quickly across room distances; and
a fine movement mechanism for moving the CT machine precisely, relative to the patient, during scanning.

In another preferred form of the invention, there is provided an imaging system, comprising:
a scanner; and
a transport mechanism mounted to the base of the scanner, wherein the transport mechanism comprises:
a gross movement mechanism for transporting the scanner relatively quickly across room distances; and
a fine movement mechanism for moving the scanner precisely, relative to the object being scanned, during scanning.

In another preferred form of the invention, there is provided a method for scanning a patient comprising:
providing an anatomical imaging system, the system comprising;
a CT machine; and
a transport mechanism mounted to the base of the CT machine, wherein the transport mechanism comprises:
a gross movement mechanism for transporting the CT machine relatively quickly across room distances; and
a fine movement mechanism for moving the CT machine precisely, relative to the patient, during scanning;
transporting the CT machine to the patient across room distances, using the gross movement mechanism; and
scanning the patient while moving the CT machine precisely, relative to the patient, with the fine movement mechanism.

In another preferred form of the invention, there is provided a method for scanning a patient, comprising:
moving a CT machine across room, distances to the patient; and
scanning the patient while moving the CT machine precisely relative to the patient during scanning.

In another preferred form of the invention, there is provided a method for scanning an object, comprising:
moving a scanner across room distances to the the object; and
scanning the object while moving the scanner precisely relative to the object during scanning.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

CT Machine 5

Figure 1:
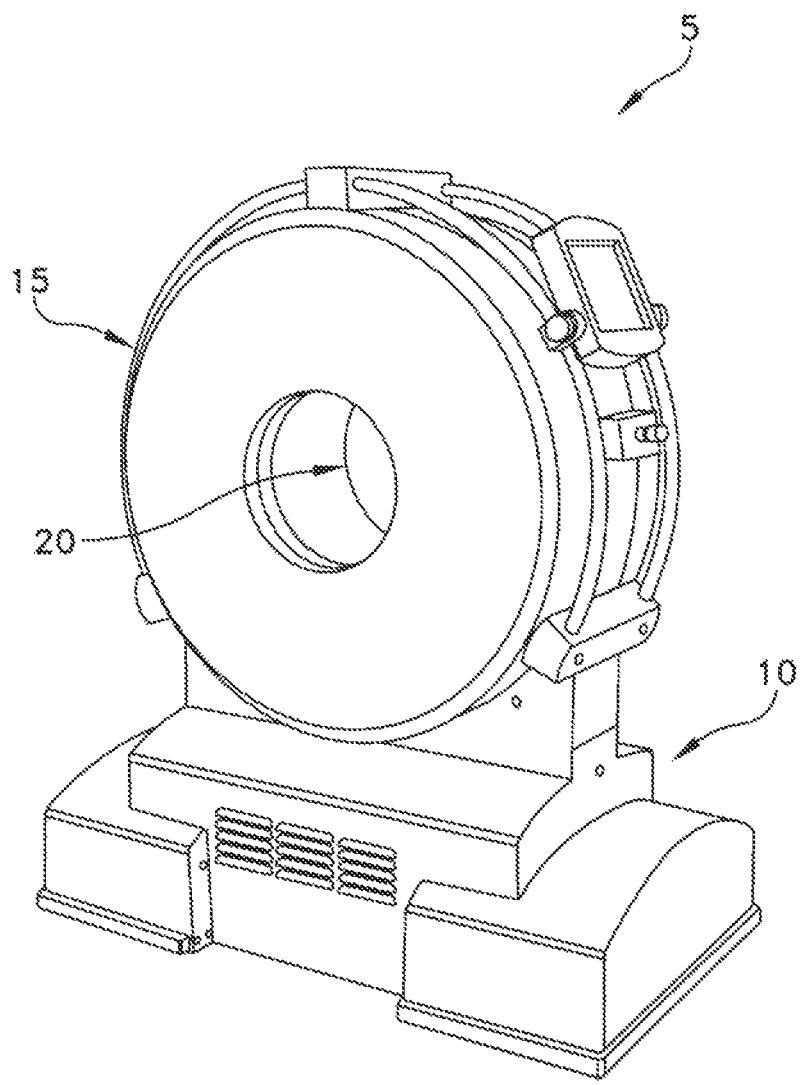
FIGS. 1-6 are a series of views showing the exterior of a novel CT machine formed in accordance with the present invention.
Figure 2:
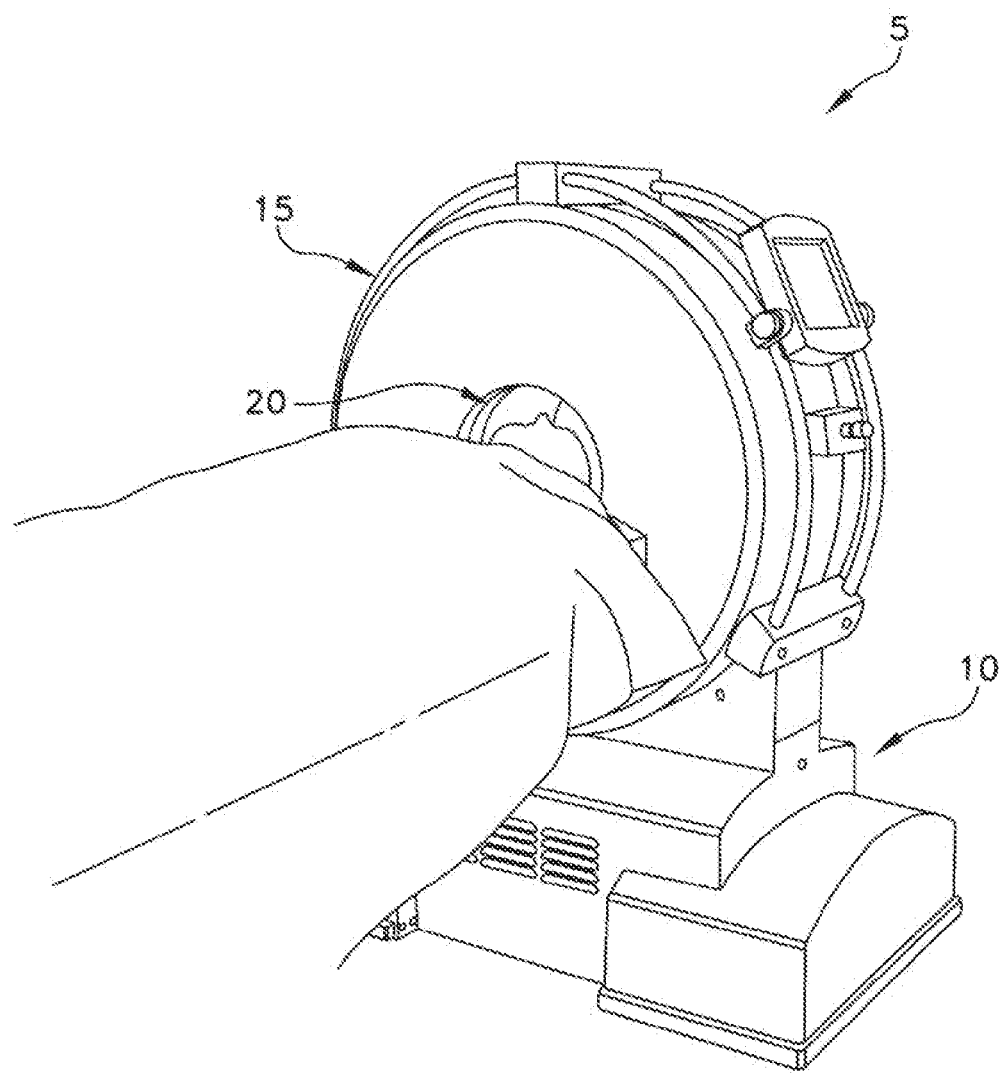
Figure 3:
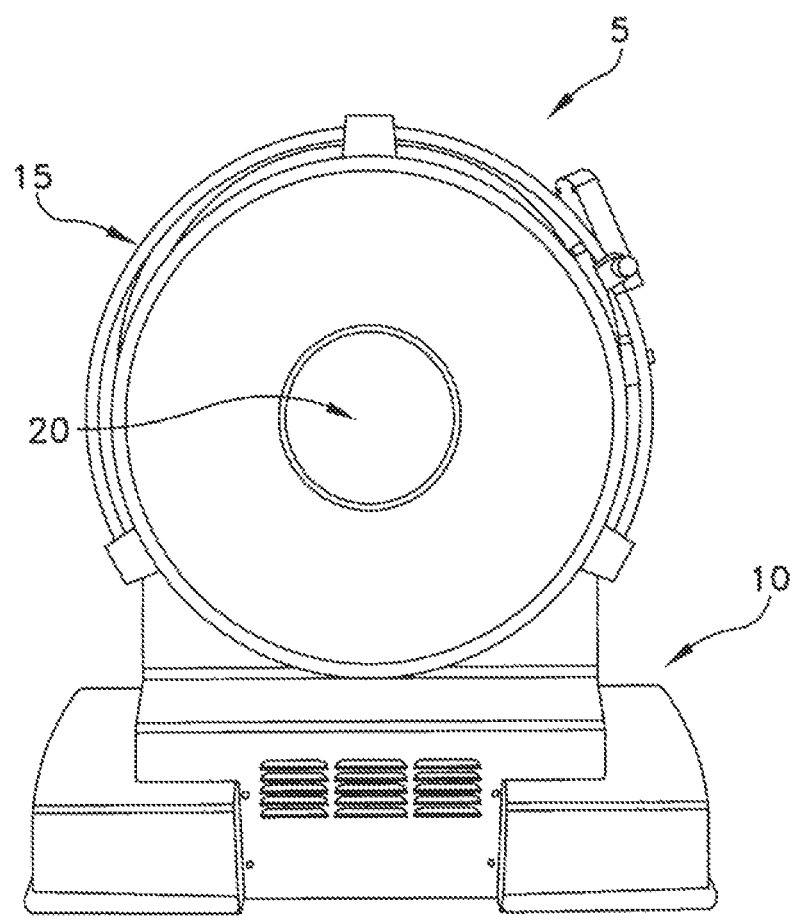
Figure 4:
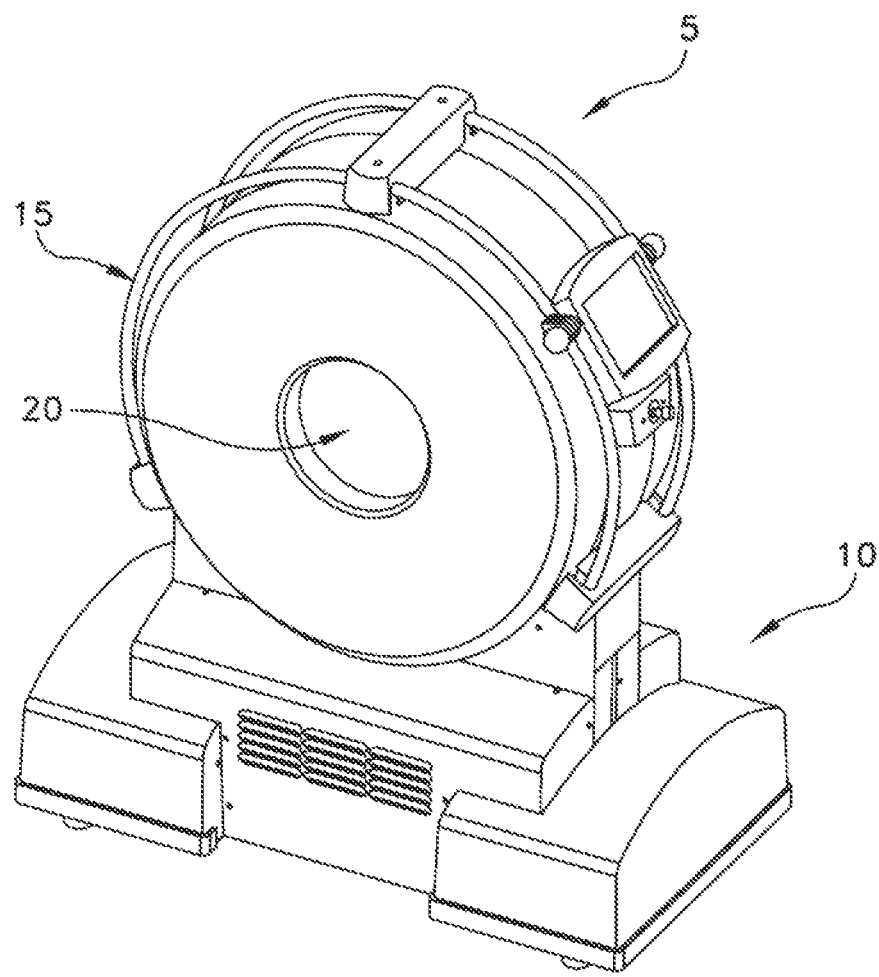
Figure 5:
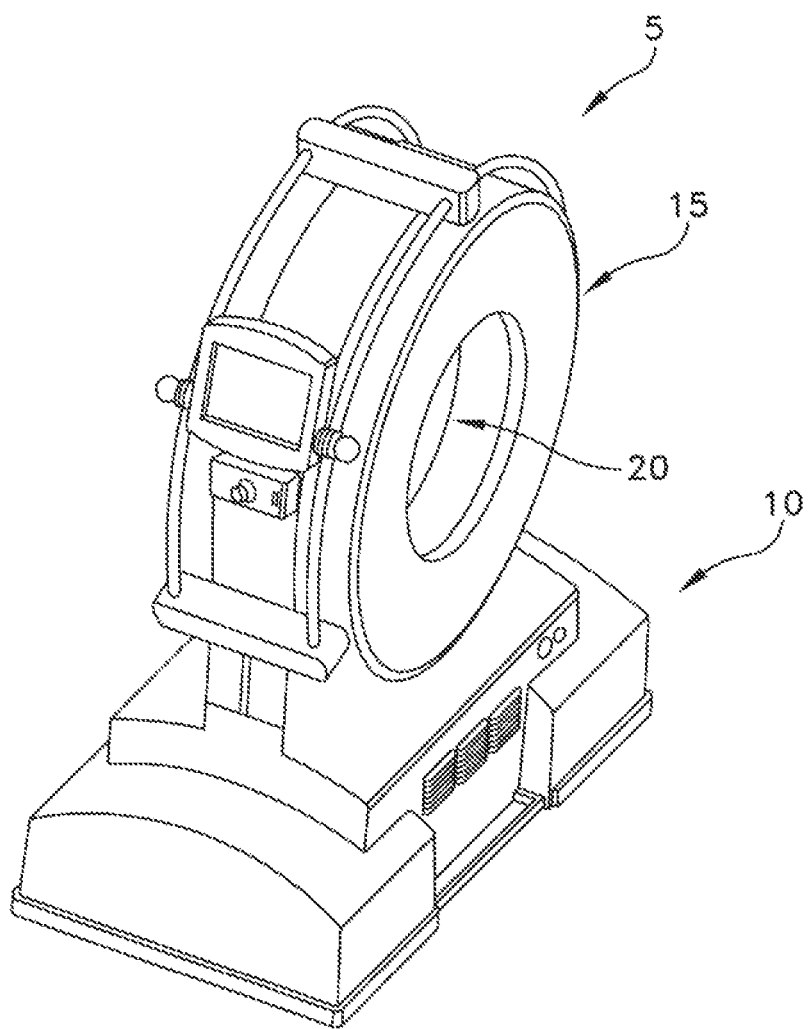
Figure 6:
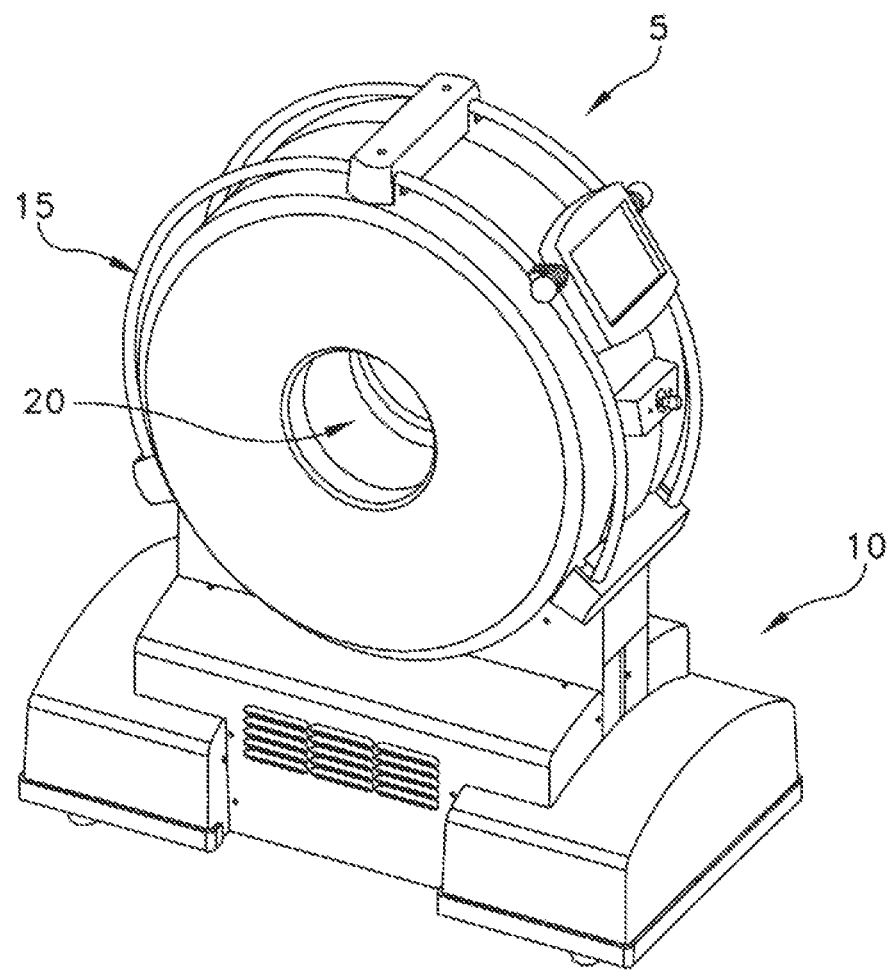

Looking first at FIGS. 1-6, there is shown a novel CT machine 5 formed in accordance with the present invention. CT machine 5 generally comprises a base 10 which supports a torus 15. Torus 15 defines a center opening 20. Base 10 and torus 15 together comprise the CT scanning apparatus which is used to scan the patient anatomy positioned in center opening 20. Such scanning apparatus typically comprises a rotating X-ray source and X-ray detector, and various electronic hardware and software for controlling the apparatus and processing the acquired data so as to generate the CT scans. Such scanning apparatus may foe of the sort well known in the art.

CT machine 5 also comprises the novel transport mechanism 100 which will hereinafter be discussed.

Transport Mechanism 100

As noted above, CT machine 5 is intended to be moved to the patient, and then scan the patient while the patient remains stationary on their gurney.

Figure 7:
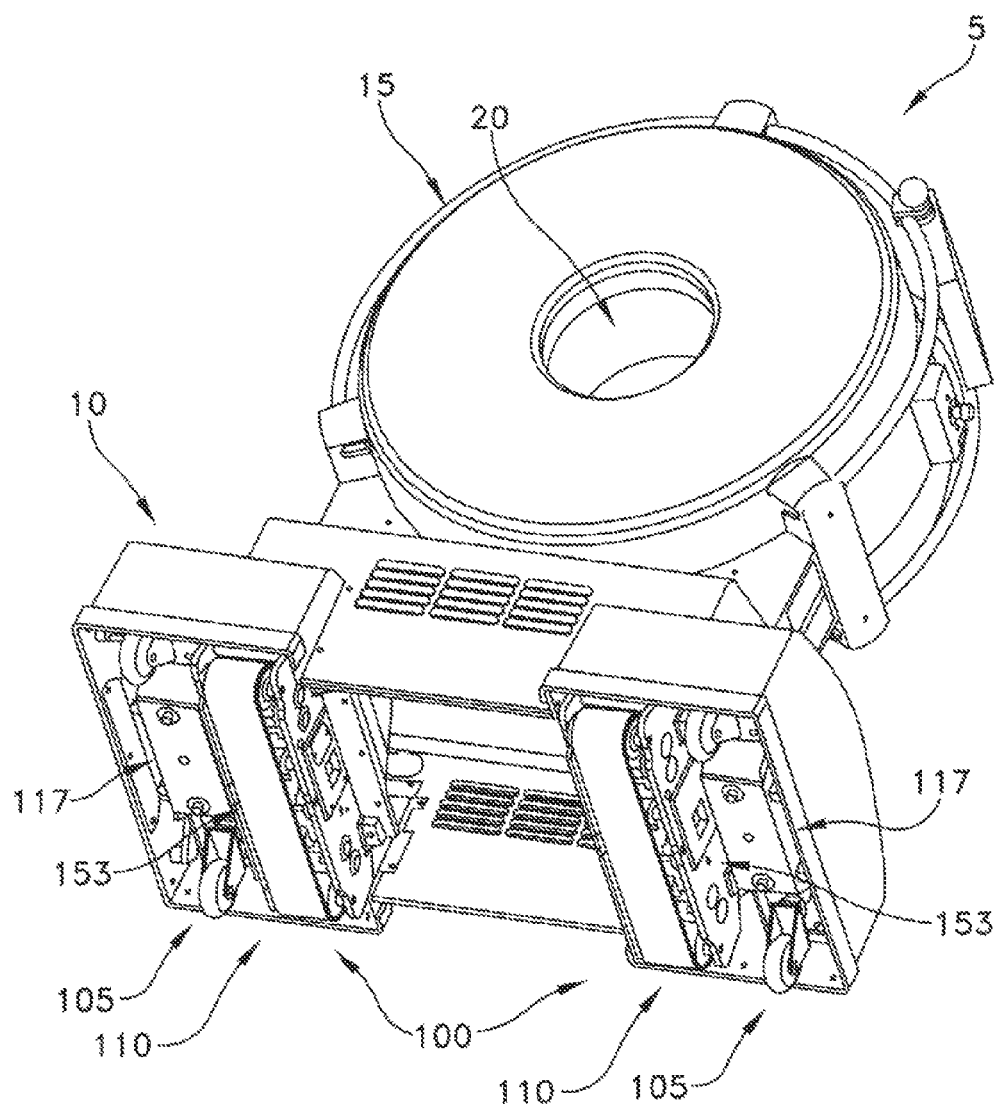
FIG. 7 is a bottom view of the CT machine showing its novel transport mechanism.

To this end, in one preferred form of the invention, and looking now at FIG. 7, CT machine 5 preferably comprises a transport mechanism 100 which comprises two different mechanisms for moving CT machine 5: (i) a gross movement mechanism 105 for transporting CT machine 5 quickly across significant distances (e.g., across a room to the patient); and (ii) a fins movement mechanism 110 for moving CT machine 5 precisely across small distances (e.g., relative to the patient during scanning). As will hereinafter foe discussed, fine movement mechanism 110 preferably comprises the aforementioned centipede belt drive for precisely moving the CT machine relative to the patient during scanning.

Figure 8:
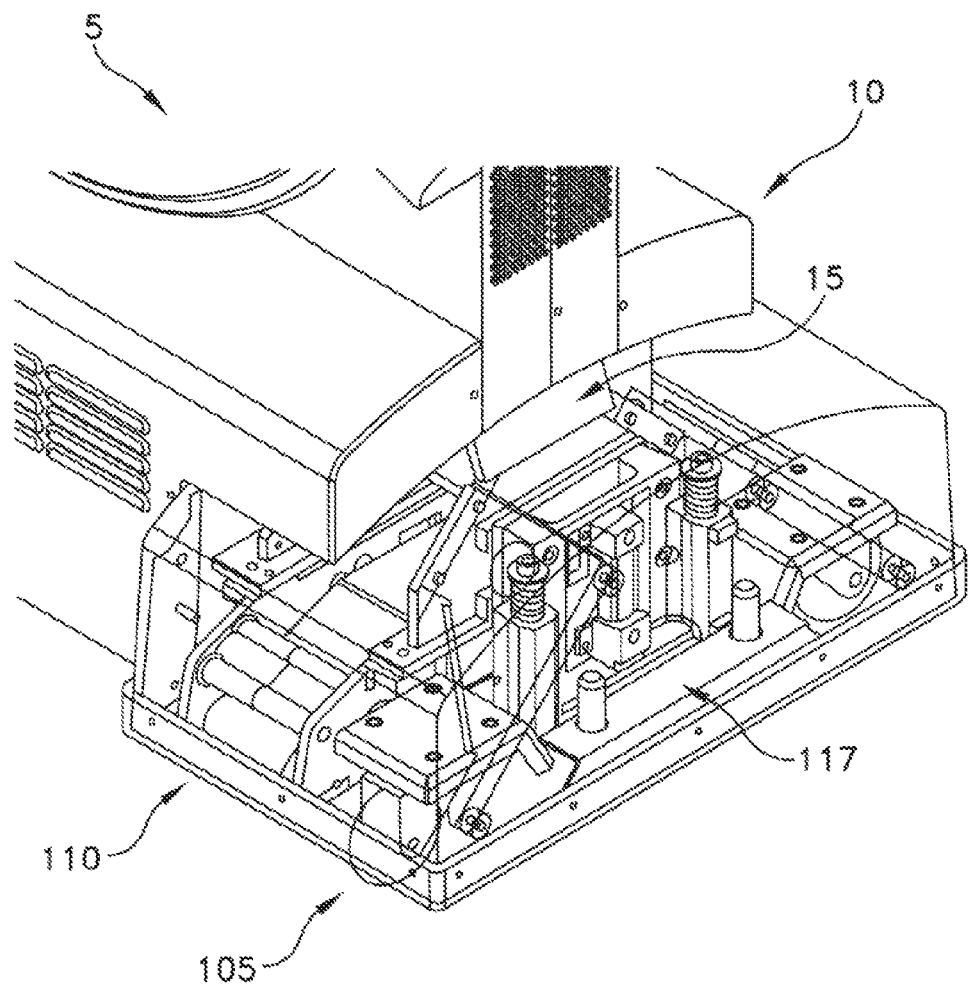
FIGS. 8-10 show the CT machine's gross movement mechanism and fine movement mechanism secured to the frame of the CT machine.
Figure 9:
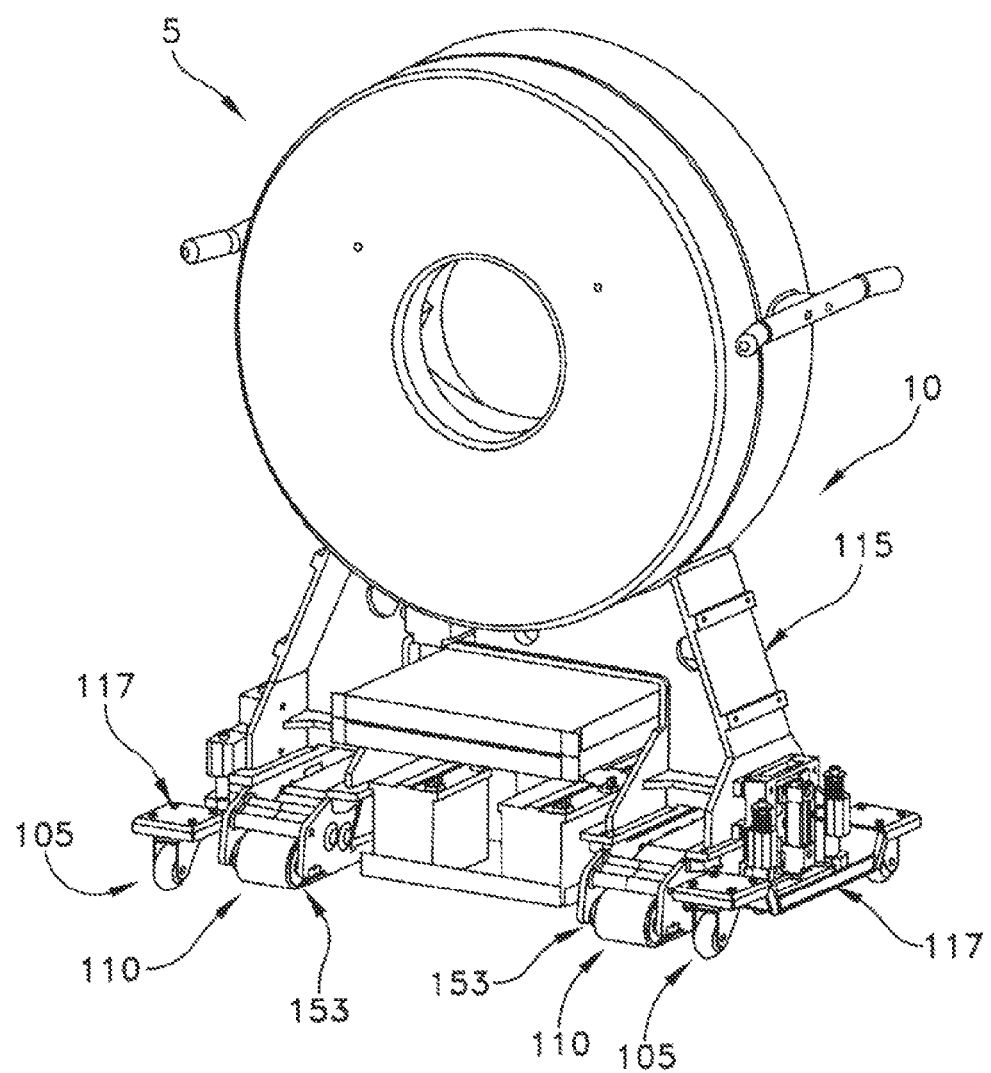
Figure 10:
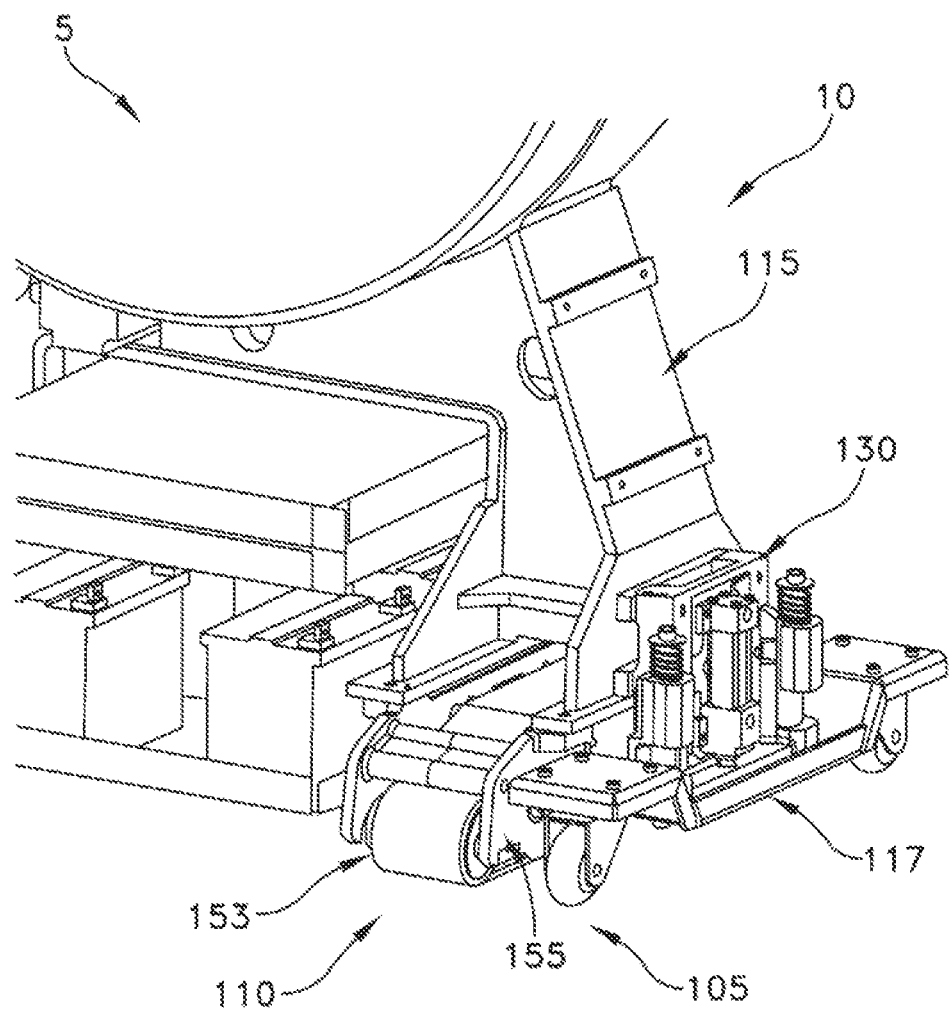
Figure 11:
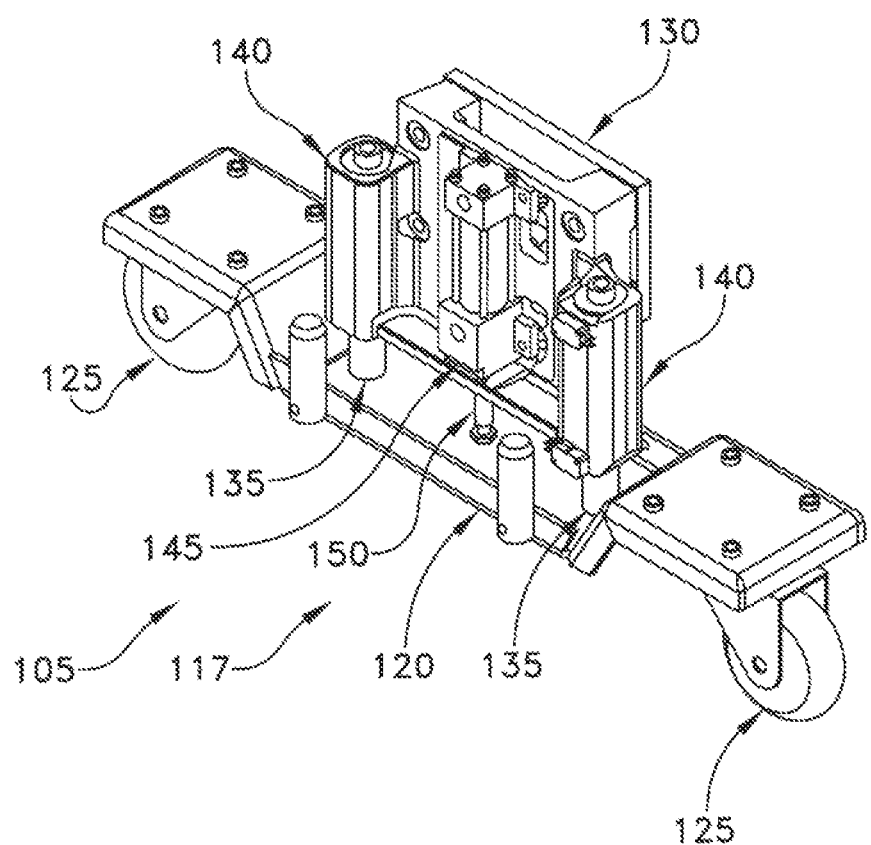
FIGS. 11-14 show details of the construction of the CT machine's gross movement mechanism.
Figure 12:
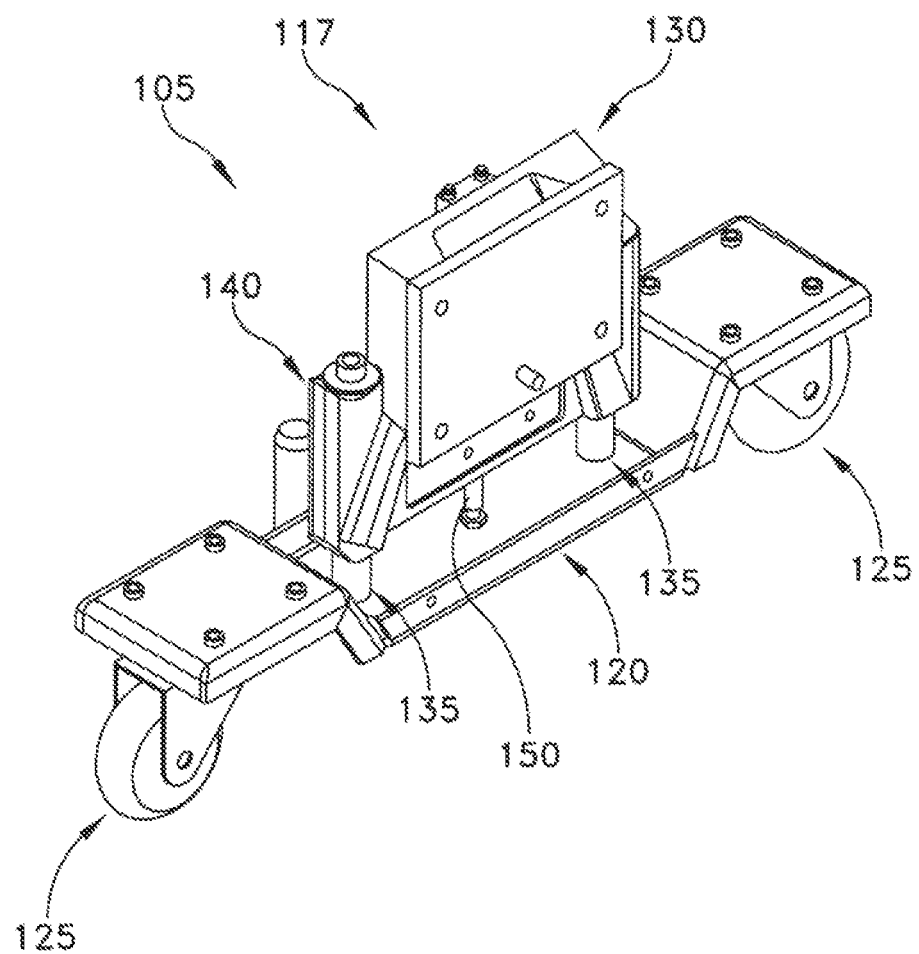
Figure 13:
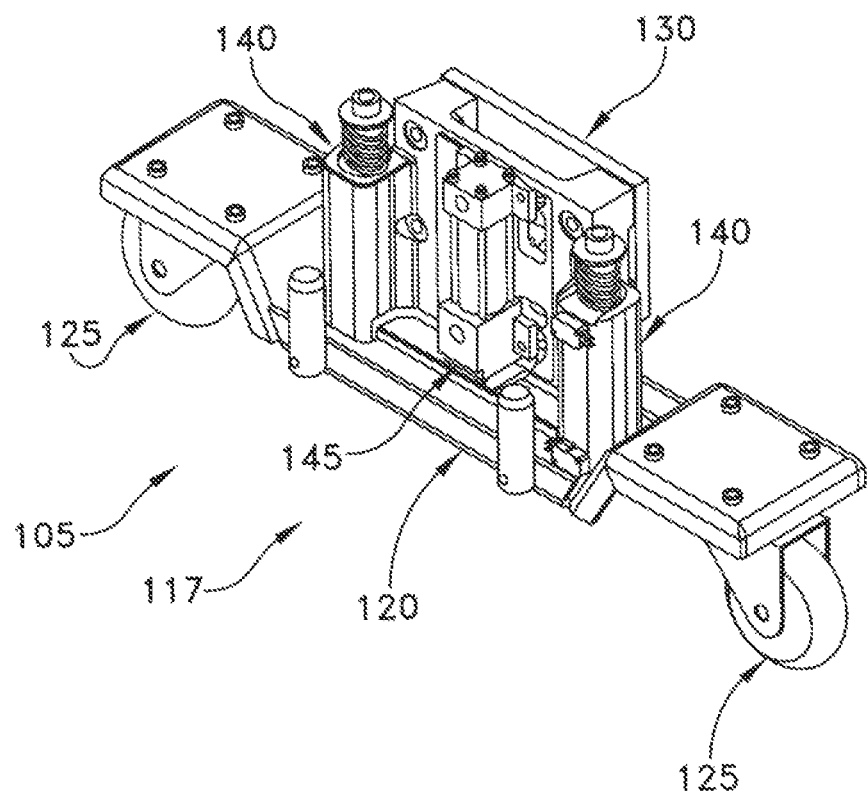
Figure 14:
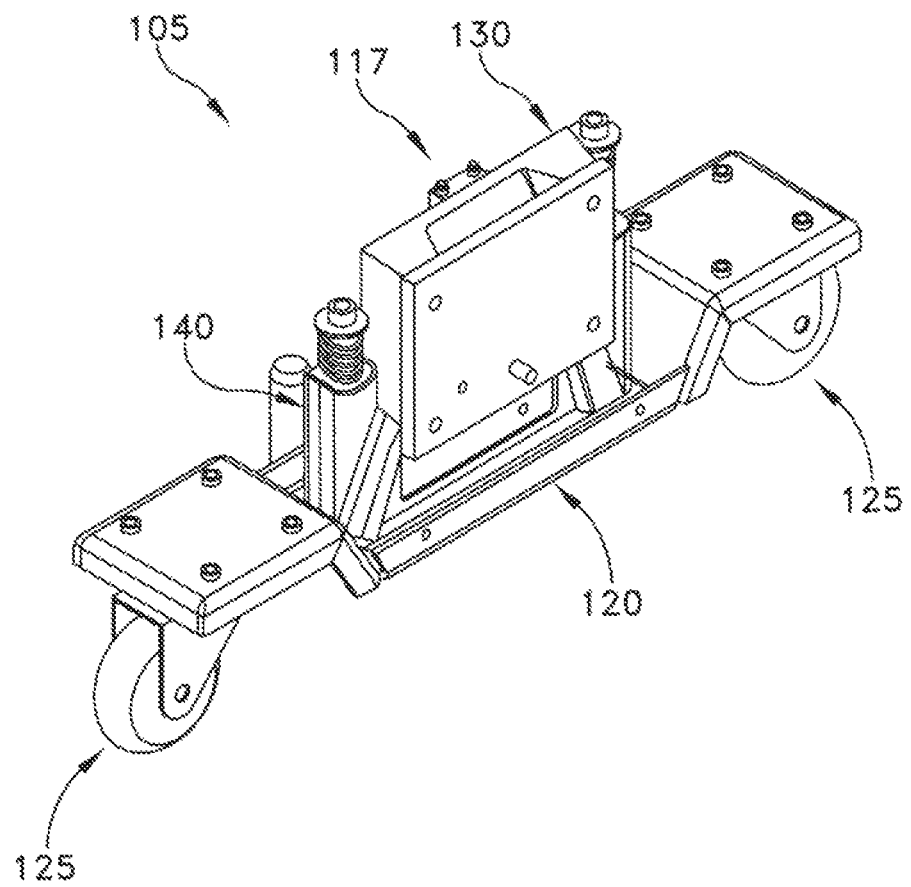
Figure 15:
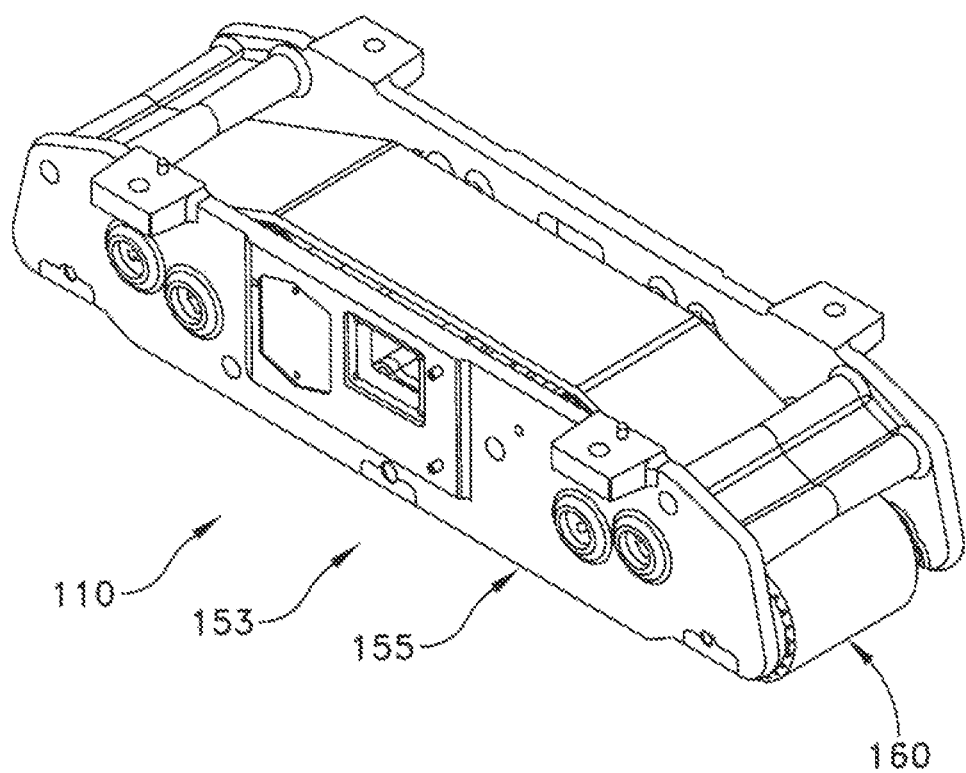
FIGS. 15-25 show details of the construction of the CT machine's fine movement mechanism.
Figure 16:
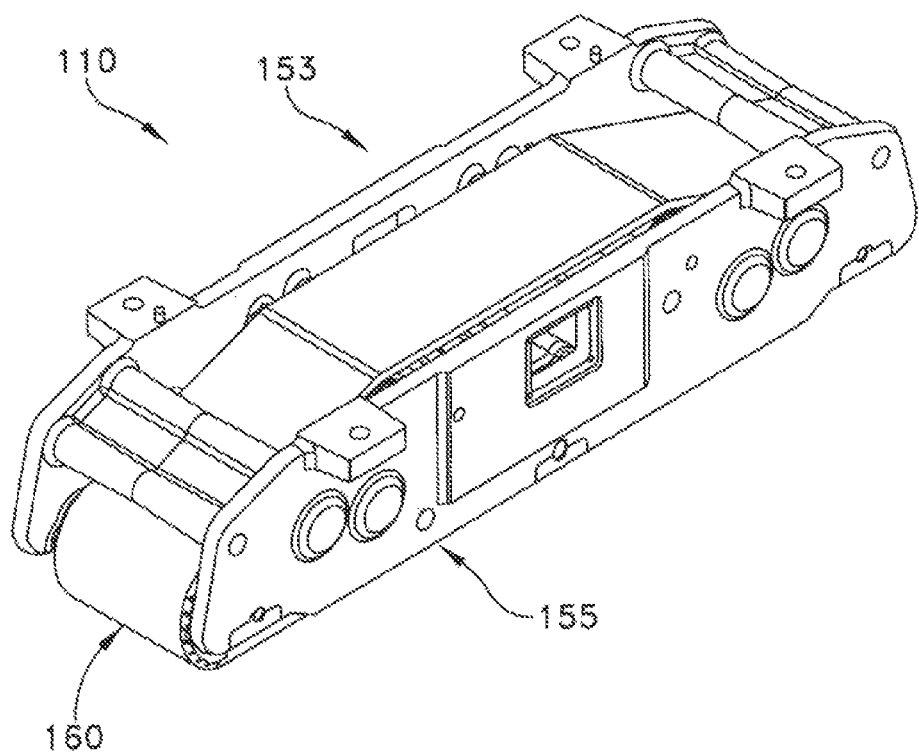
Figure 17:
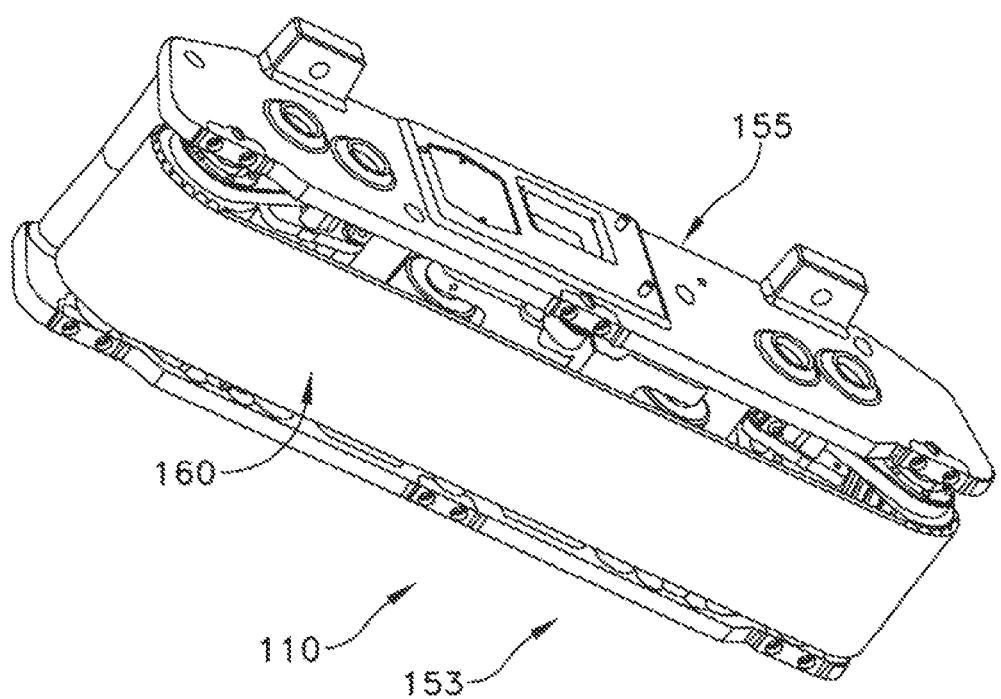
Figure 18:
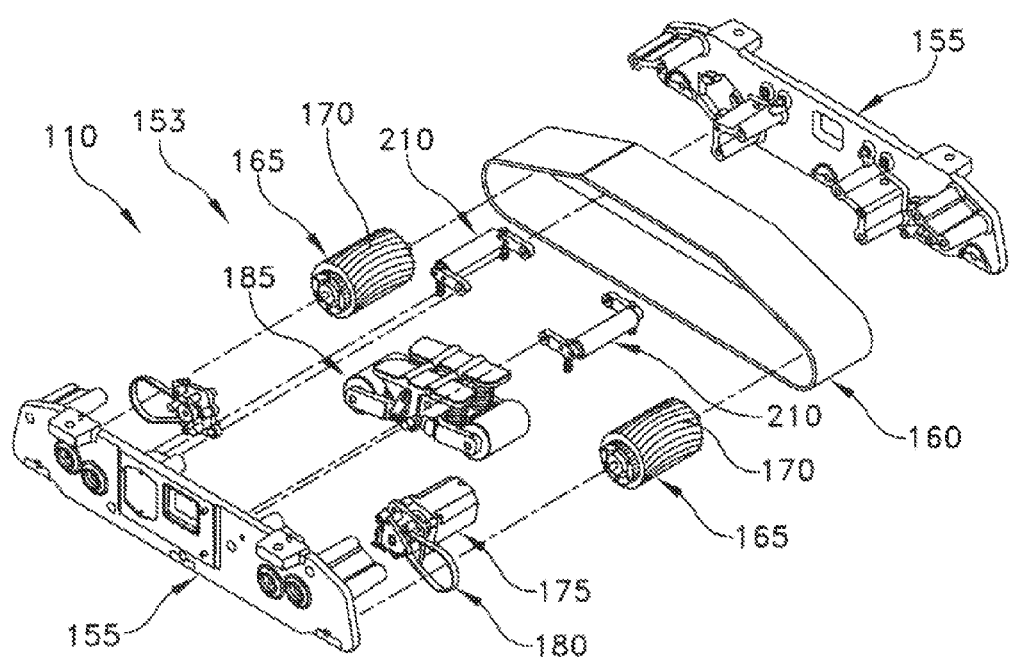
Figure 19:
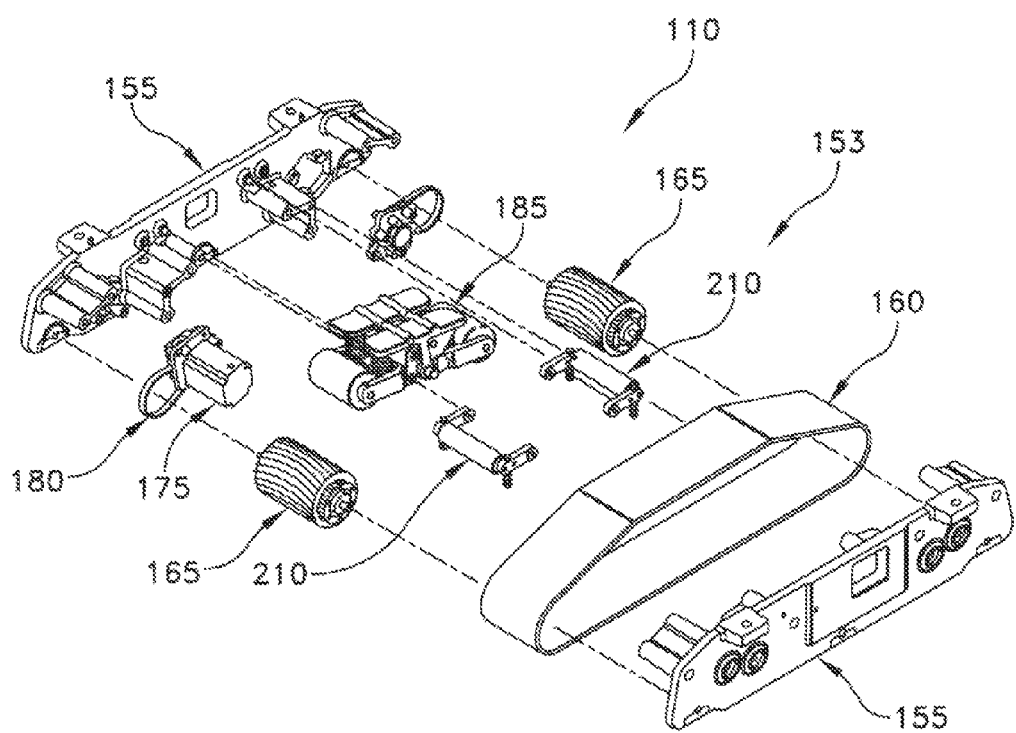
Figure 20:
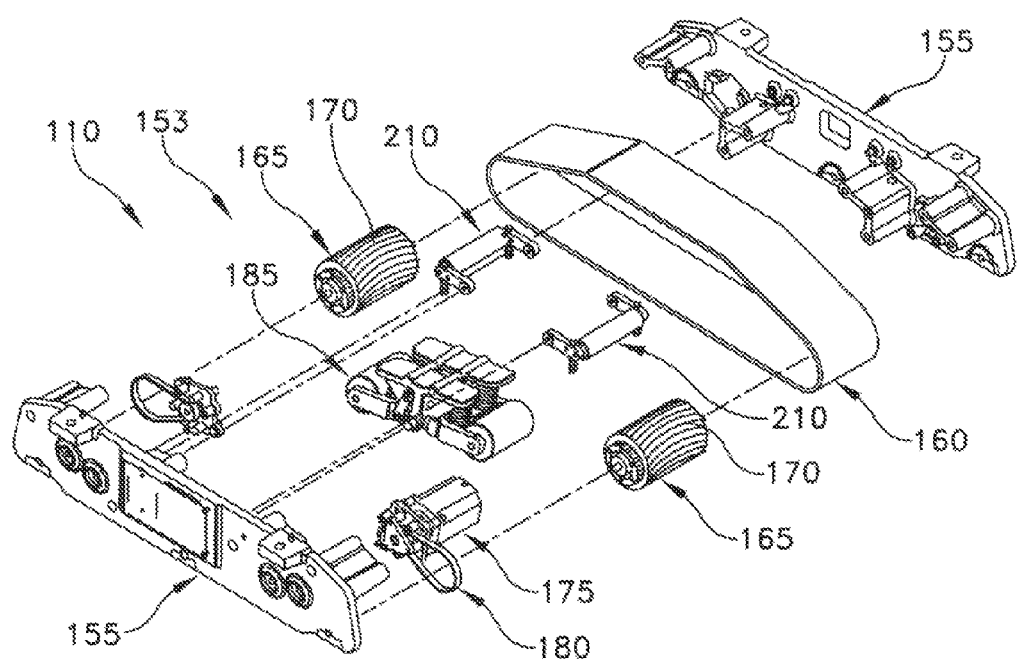
Figure 21:
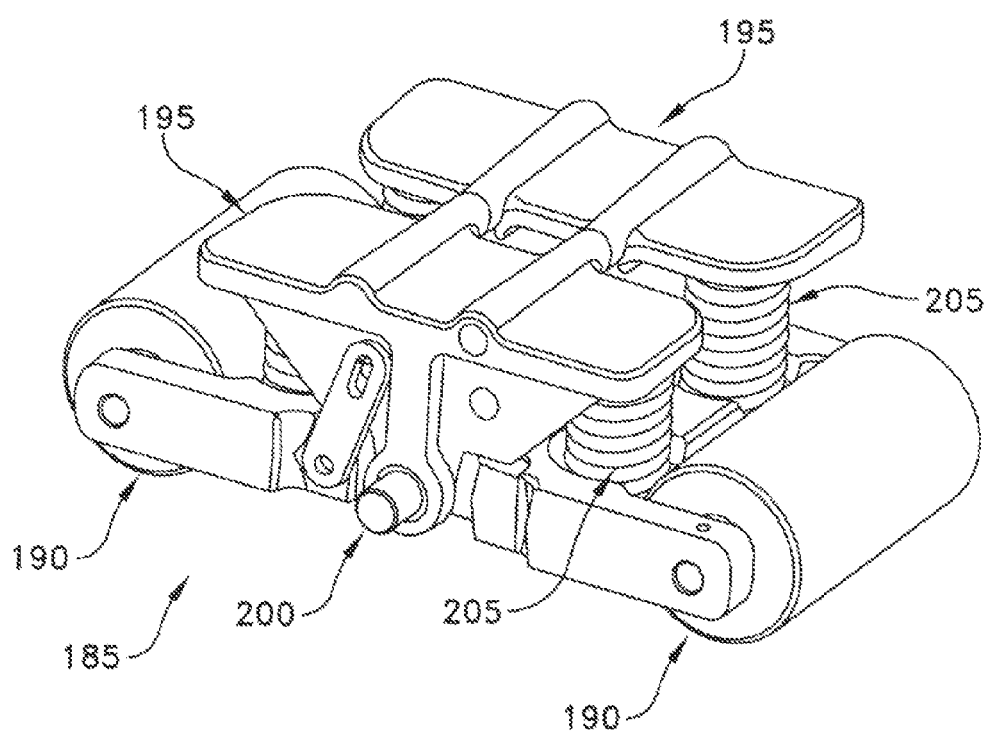
Figure 22:
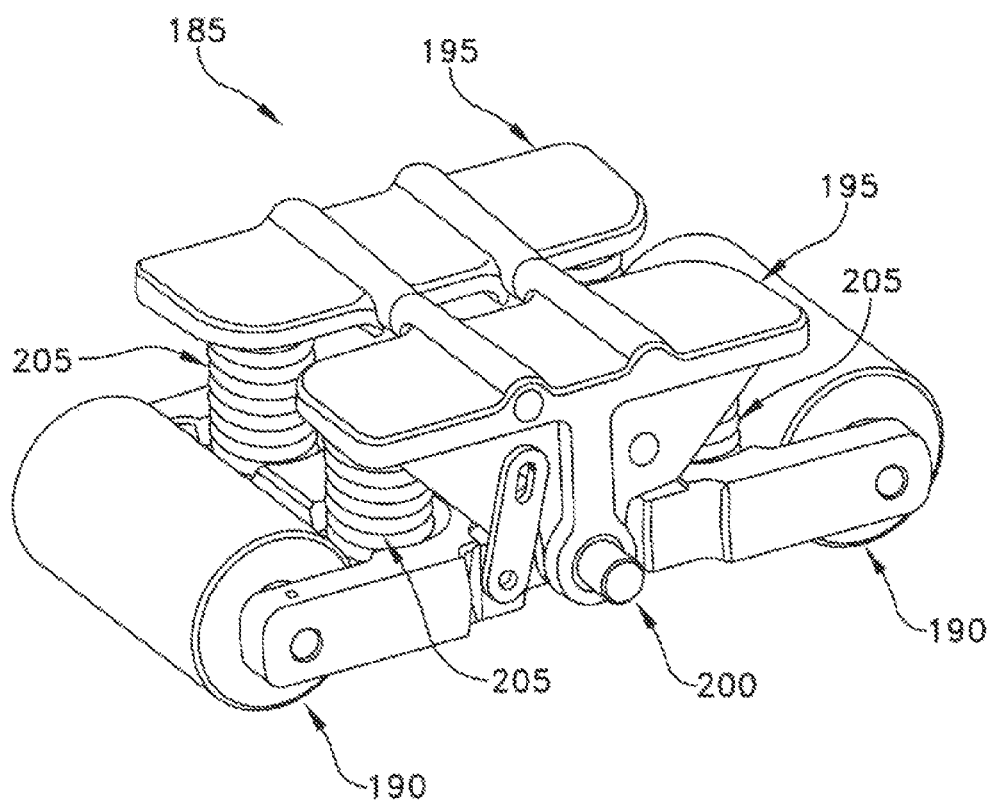
Figure 23:
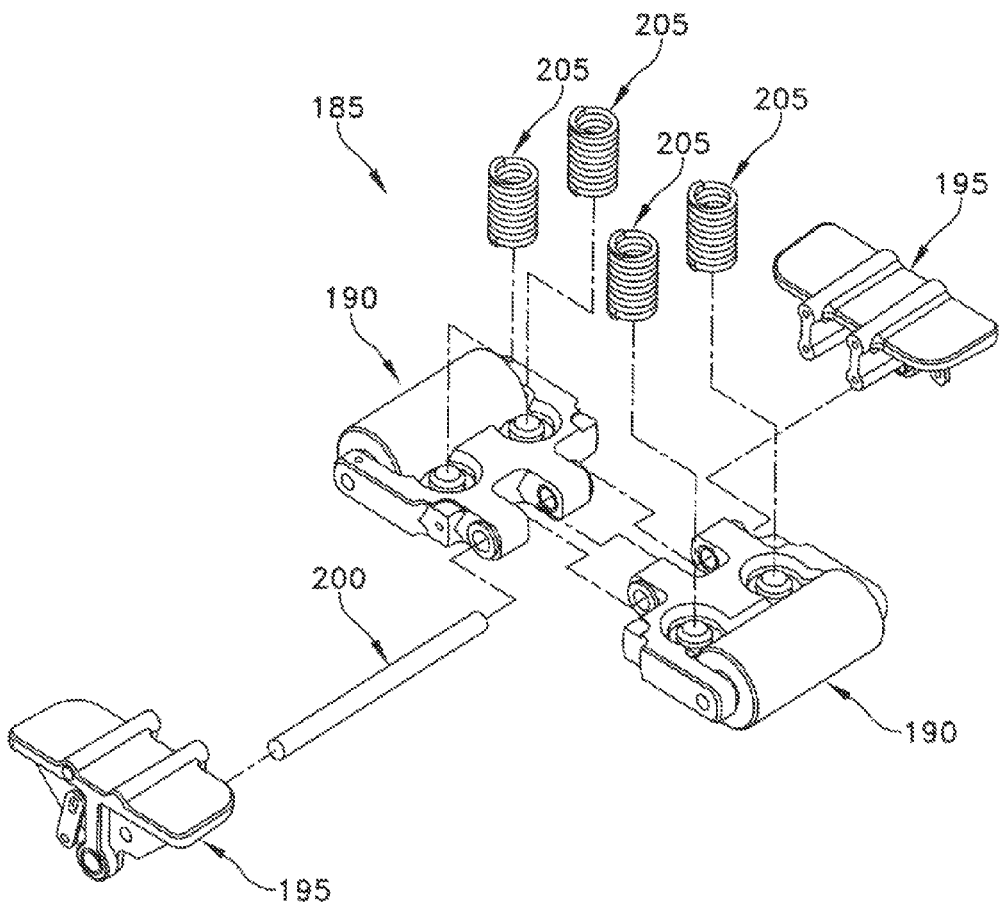
Figure 24:
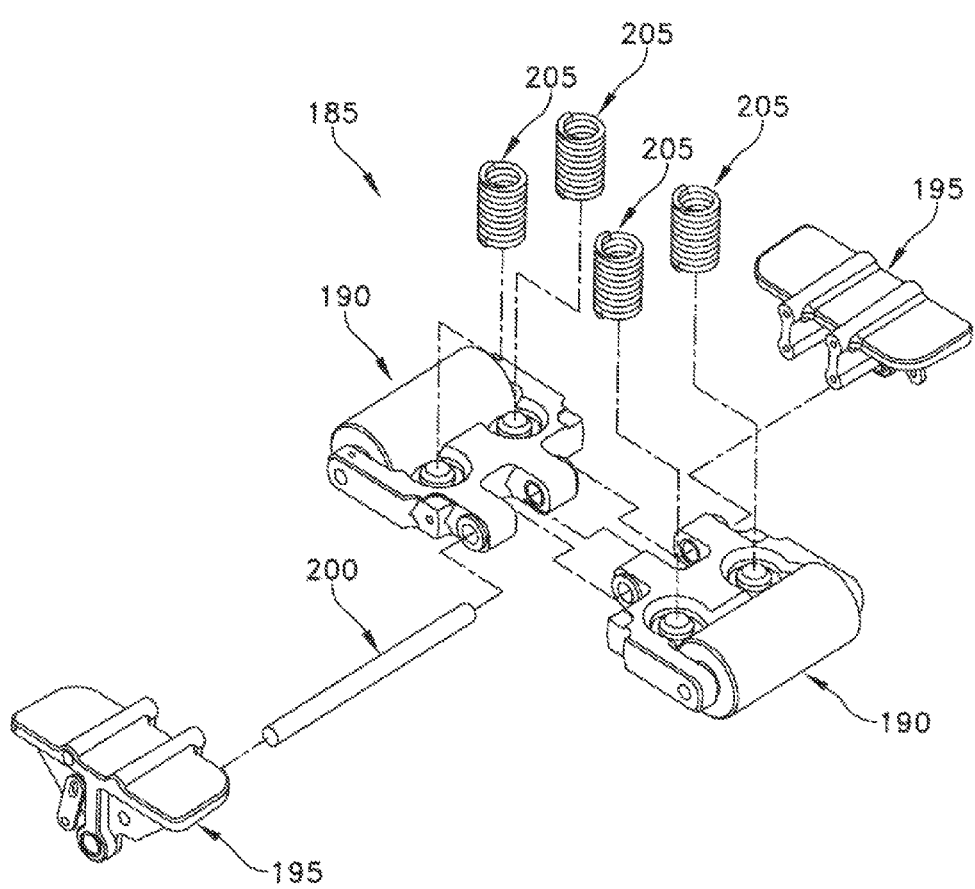
Figure 25:
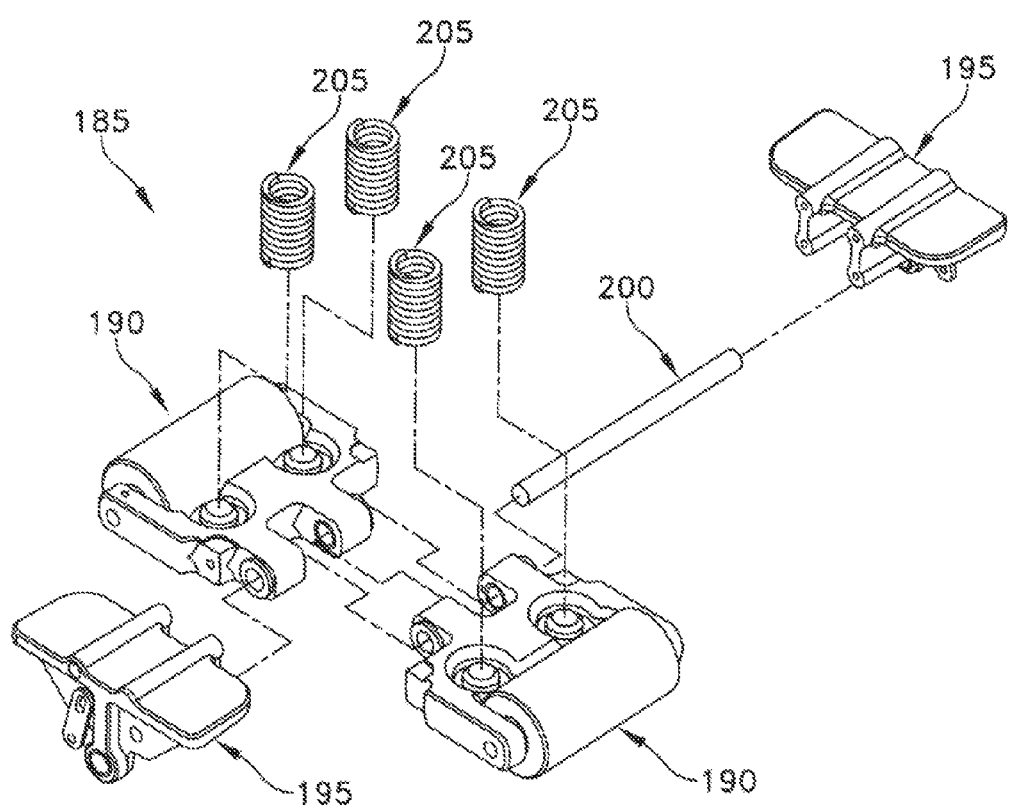

As seen in FIGS. 8-10, gross movement mechanism 105 and fine movement mechanism 110 are both secured to the frame 115 of base 10 so that they can, alternatively, support CT machine 5, Gross Movement Mechanism 105

Gross movement mechanism 105 is used to transport CT machine 5 quickly across significant distances (e.g., across a room to the patient). More particularly, and looking now at FIGS. 8-14, gross movement mechanism 105 preferably comprises two identical, spaced-apart caster units 117 which cooperate to form the gross movement mechanism 105.

Each caster unit 117 comprises a chassis 120 having a pair of casters 125 rotatably mounted thereto. Chassis 120 is movably mounted to a support block 130, and support block 130 is in turn secured to frame 115. More particularly, chassis 120 is movably mounted to support block 130 by means of a pair of slide rods 135 and support block 130 are slidably received in slide housings 140 which are secured to support block 130. An actuator (hydraulic or otherwise) 145, which is mounted to support block 130, has its actuator rod 150 engaging chassis 120. As noted above, support block 130 is secured to frame 115 of CT machine 5.

As a result of this construction, when it is desired to move CT machine 5 about on gross movement mechanism 105, gross movement mechanism 105 is operated as follows. The two caster units 117 are operated in a coordinated fashion so that their actuators (hydraulic or otherwise) 145 extend their actuator rods 150 so as to cause chassis 120 to project downward from support blocks 130, whereby to cause the casters 125 to engage the floor and support CT machine 5 on the casters 125. CT machine 5 can then be maneuvered about a room on the casters 125. When it is desired to use the CT machine 5 for scanning, the gross movement mechanism 105 is operated as follows. The two caster units 11 are operated in a coordinated fashion so that their actuators (hydraulic or otherwise) 145 retract their actuator rods 150 so as to cause chassis 120 to return towards support blocks 130, whereby to seat fine movement mechanism 110 of CT machine 5 securely on the floor.

In one configuration, gross movement mechanism 105 comprises two identical caster units 117, with one caster unit 117 located on each side of the patient. Alternatively, more than two caster units 11 may be provided (e.g., three or four), and they may be distributed about base 10 of CT machine 5 in any desired configuration.

Fine Movement Mechanism 110

Fine movement mechanism 110 is used to move CT machine 5 precisely relative to the patient during scanning. More particularly, and looking now at FIGS. 7 and 9, fine movement mechanism 110 preferably comprises two identical, spaced-apart centipede belt drive units 153 which cooperate to form the fine movement mechanism 110.

Looking next at FIGS. 15-25, each centipede belt drive unit 153 comprises a chassis 155 which is secured to frame 115. Chassis 155 preferably comprises two halves (FIG. 18) which are secured together to form a single housing with an interior space. Chassis 155 has a belt 160 drivably mounted thereto. More particularly, chassis 155 comprises a pair of drive gears (sometimes referred to as a timing pulley) 165 which are rotatably mounted to chassis 155. Drive gears 165 comprise teeth 170 which engage counterpart ribs (not shown) formed on the interior of belt 160, such that when drive gears 165 are rotated, their rotational motion is transferred to belt 160. Preferably teeth 170 have an arched configuration, so as to provide a uniform engagement between adjacent teeth and the drive belt, thereby allowing precision transfer of motion between the drive gear and the drive belt. One or more motors 175 are secured to chassis 155. Preferably motors 175 are located inside the centipede belt drive unit to save space. A transmission belt 180 connects the drive shaft of motor 175 to at least one of the drive gears 165, whereby the one or more motors 175 can be used to turn belt 160 and thereby drive the unit.

A suspension unit 185, such as the one shown in FIGS. 18-25, or another suspension unit of the sort well known in the belt drive art, is preferably secured to chassis 155 within the interior of belt 160 so as to distribute the load of CT machine 5 across a plurality of rollers and onto the belt 160. In one preferred construction, suspension unit 185 comprises (FIGS. 21-25) a pair of roller assemblies 190 balanced with a pair of rockers 195 which are mounted on an axle 200 and balanced, with four springs 205. Additional suspension rollers (e.g., rollers 210 in FIGS. 18-20) may also be provided if desired.

As a result of this construction, when it is desired to move CT machine 5 on fine movement mechanism 110, CT machine 5 is lowered onto fine movement mechanism 105 (i.e., by retracting the casters 125 of gross movement mechanism 105), and then fine movement mechanism 110 is operated as follows. The two centipede belt drive units 153 are operated in a coordinated fashion so that their motors 175 rotate drive gears 165, whereby to turn belts 160 and thereby precisely advance CT machine 5 (e.g., relative to a patient).

The centipede belt drive unit 153 is designed to move the CT machine relative to the patient in one of two motions; (1) indexed movement using discrete steps for slice scanning; and (2) smooth movement using substantially continuous motion for helical scanning. The centipede belt drive unit 153 achieves this through the use of the aforementioned floor-engaging drive belts 160 which provide the necessary precision movement and repeatability The centipede belt drive system is preferably configured to allow multi-directional patient scanning, i.e., scanning in both forward and backward directions.

In a preferred embodiment of the invention, two independent centipede belt drive units 153 are used, one on each side of the patient. The two centipede belt drive units are driven in a coordinated fashion so as to effect the precise movement desired. In this respect it should be appreciated that, due to the use of two independent belt drives, differences in components or external conditions (e.g., floor tilt) may create a yawing effect. This is resolved by driving each belt separately at an appropriate rate.

A feedback system is preferably used to ensure that each centipede belt drive unit 153 is moving at the desired speed. An encoder device (e.g., an optical encoder or a rotary potentiometer or other device) may be used to determine the rate of drive gear movement so as to regulate belt movement. In this respect it should be appreciated that, in view of the very small movements associated with CT scanning, hysteresis problems may arise with the drive belts 160. The encoder device may also be used to identify and compensate for any such hysteresis.

In one configuration, the fine movement mechanism 105 comprises two identical centipede belt drive units 153, with the two identical drives straddling the patient. Alternatively, the CT machine could be provided with wheels on each side of the patient, and a single centipede belt drive unit 153 could be provided to move the wheeled assembly during scanning movement.

Use

In accordance with the present invention, transport mechanism 100 can be used to move CT machine 5 as follows. Initially, CT machine 5 is raised on its gross movement mechanism 105 by causing actuators (hydraulic or otherwise) 145 to extend their actuator rods 150, whereby to cause casters 125 to engage the floor and support CT machine 5 on the casters 125. CT machine 5 can then be maneuvered about a room on its casters 125, i.e., so that a patient lying on a gurney may foe positioned within the center opening 20 of CT machine 5 without moving the patient off the gurney. Thereafter, gross movement mechanism 105 is operated so that the caster units 11 retract their actuator rods 150 so as to cause chassis 120 to return towards their support blocks 130, whereby to permit the drive belts 160 of fine movement mechanism 110 to engage the floor. Thereafter, when scanning is commenced, motors 175 are used to precisely advance belt 160, and hence CT machine 5, relative to the patient during scanning.

Thus, in one preferred form of the invention, the fine movement mechanism 110 operates only during the scanning process. More particularly, prior to scanning, the CT machine is moved to the patient on gross movement mechanism 105; thereafter, the fine movement mechanism 105 engages the floor and operates during scanning to move the CT machine relative to the patient during the scanning process. Alternatively, where fine movement mechanism 110 is capable of reasonably rapid rates of speed, gross movement mechanism 105 may be omitted entirely and only fine movement mechanism 110 provided.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines used to scan inanimate objects. Furthermore, the present invention may be used with non-CT-type scanning systems. In essence, the present invention has application to any scanning device which requires that the scanning apparatus be precisely moved relative to the scanned object. Thus, for example, the present invention may foe used in conjunction with other types of scanners.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An imaging system for imaging an object, comprising:
a scanner; and
a transport mechanism mounted to a base of the scanner, wherein the transport mechanism comprises a crawl drive for directly engaging a floor supporting the imaging system and crawling along the floor supporting the imaging system so as to index the scanner relative to an object during scanning of the object;
wherein the transport mechanism further comprises a gross movement mechanism for transporting the scanner relatively quickly across room distances;
wherein the gross movement mechanism comprises an actuator for: (i) extending portions of the gross movement mechanism below portions of the crawl drive drive whereby the scanner will be supported by portions of the gross movement mechanism; and (ii) retracting portions of the gross movement mechanism above portions of the crawl drive whereby the scanner will be supported by portions of the crawl drive.

2. An imaging system according to claim 1 wherein the crawl drive is configured to index the scanner relative to the object using discrete steps, whereby to enable slice scanning.

3. An imaging system according to claim 1 wherein the crawl drive is configured to index the scanner relative to the object using substantially continuous movement, whereby to enable helical scanning.

4. An imaging system according to claim 1 wherein the crawl drive comprises at least one centipede belt drive unit.

5. An imaging system according to claim 1 wherein the gross movement mechanism comprises at least one caster.

6. An imaging system according to claim 1 wherein the scanner comprises a CT machine.

7. An imaging system according to claim 1 wherein the object comprises a patient.

8. A method for scanning an object, the method comprising:
providing an imaging system for imaging an object, comprising:
a scanner; and
a transport mechanism mounted to a base of the scanner, wherein the transport mechanism comprises a crawl drive for directly engaging a floor supporting the imaging system and crawling along the floor supporting the imaging system so as to index the scanner relative to the object during scanning of the object;
wherein the transport mechanism further comprises a gross movement mechanism for transporting the scanner relatively quickly across room distances;
wherein the gross movement mechanism comprises an actuator for: (i) extending portions of the gross movement mechanism below portions of the crawl drive whereby the scanner will be supported by portions of the gross movement mechanism; and (ii) retracting portions of the gross movement mechanism above portions of the crawl drive whereby the scanner will be suppported by portions of the crawl drive; and
scanning the object while moving the scanner precisely relative to the object, using the crawl drive, during scanning.

9. A method according to claim 8 wherein the crawl drive is configured to index the scanner relative to the object using discrete steps, whereby to enable slice scanning.

10. A method according to claim 8 wherein the crawl drive is configured to index the scanner relative to the object using substantially continuous movement, whereby to enable helical scanning.

11. A method according to claim 8 wherein the crawl drive comprises at least one centipede belt drive unit.

12. A method according to claim 8 wherein the gross movement mechanism comprises at least one caster.

13. A method according to claim 8 wherein the scanner comprises a CT machine.

14. A method according to claim 8 wherein the object comprises a patient.

15. An imaging system for imaging an object, comprising:
a scanner; and
a transport mechanism mounted to a base of the scanner, wherein the transport mechanism comprises a crawl drive for directly engaging a floor supporting the imaging system and crawling along the floor supporting the imaging system so as to index the scanner relative to an object during scanning of the object;
wherein the crawl drive comprises at least one centipede belt drive unit.

16. A method for scanning an object, the method comprising:
providing an imaging system for imaging an object, comprising:
a scanner; and
a transport mechanism mounted to a base of the scanner, wherein the transport mechanism comprises a crawl drive for directly engaging a floor supporting the imaging system and crawling along the floor supporting the imaging system so as to index the scanner relative to the object during scanning of the object;
wherein the crawl drive comprises at least one centipede belt drive unit; and scanning the object while moving the scanner precisely relative to the object, using the crawl drive, during scanning.

\* \* \* \* \*